United States Patent [19]

Bohen et al.

[11] Patent Number: 5,030,679

[45] Date of Patent: Jul. 9, 1991

[54] ORGANIC SULFIDE ANTIOXIDANTS AND POLYMERS STABILIZED THEREWITH

[75] Inventors: Joseph M. Bohen, King of Prussia; James L. Reilly, Towamencin, both of Pa.

[73] Assignee: Atochem North America, Inc., Philadelphia, Pa.

[21] Appl. No.: 429,885

[22] Filed: Oct. 31, 1989

[51] Int. Cl.$^5$ .................. C08K 5/36; C07C 323/12
[52] U.S. Cl. ........................... 524/58; 524/58; 536/18.3; 536/14; 568/50
[58] Field of Search .............. 524/367, 368, 377, 378, 524/58; 536/18.3, 4; 568/46, 49, 50, 51, 57, 613, 624, 625, 39, 616

[56] References Cited

U.S. PATENT DOCUMENTS

| | | | |
|---|---|---|---|
| 2,326,483 | 8/1943 | Moran | 568/49 |
| 2,352,078 | 6/1944 | Coleman et al. | 568/39 |
| 2,522,590 | 9/1950 | Vaughan et al. | 568/39 |
| 2,582,605 | 1/1952 | Richter et al. | 568/39 |
| 2,995,539 | 8/1961 | Barker et al. | 524/368 |
| 3,180,850 | 4/1965 | Schooten et al. | 524/324 |
| 3,258,493 | 6/1966 | Braus et al. | 568/57 |
| 3,293,209 | 12/1966 | Baldwin et al. | 524/333 |
| 3,574,165 | 4/1971 | Braus et al. | 524/326 |
| 3,652,680 | 3/1972 | Buchholz et al. | 568/57 |
| 3,737,426 | 6/1973 | Thruckmorton et al. | 536/18.3 |
| 3,772,246 | 11/1973 | Buchholz et al. | 524/392 |
| 3,823,191 | 7/1974 | Dighe | 568/62 |
| 3,997,612 | 12/1976 | Lenke et al. | 524/368 |
| 3,997,613 | 12/1976 | Lenke et al. | 524/368 |
| 4,355,185 | 10/1982 | Borgthaller et al. | 568/57 |
| 4,433,179 | 2/1984 | Lohse et al. | 568/616 |

Primary Examiner—Veronica P. Hoke
Attorney, Agent, or Firm—Panitch Schwarze Jacobs & Nadel

[57] ABSTRACT

Organic sulfide antioxidants useful for stabilizing polyolefins against oxidative and thermal degradation during processing and use represented by Formula I:

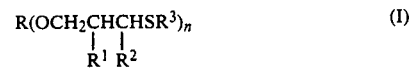

$$R(OCH_2CHCHSR^3)_n \quad\quad (I)$$
$$\phantom{R(OCH_2C}R^1\ R^2$$

wherein n is an integer of 2 to 15;

R is a substituted or unsubstituted alkyl group of 2 to 30 carbons, a substituted or unsubstituted cycloalkyl group of 5 to 20 carbons a substituted or unsubstituted alkyl group of 2 to 30 carbons where any of up to 6 carbon atoms are replaced with an O or S heteroatom, a substituted or unsubstituted cycloalkyl group of 5 to 20 carbons where any of up to 6 carbon atoms are replaced with an O or S heteroatom, with the proviso that the heteroatoms must be separated from each other and from the portion of the compound to which the R group is bonded by at least one carbon atom, the substituents for R being —OH, —SR$^4$ or —OR$^4$, wherein R$^4$ is an alkyl group of 1 to 30 carbons or a cycloalkyl group of 5 to 20 carbons;

R$^1$ and R$^2$ are independently H or an alkyl group of 1 to 4 carbons; and

R$^3$ is an alkyl group of 1 to 24 carbons or a cycloalkyl group of 5 to 20 carbons.

23 Claims, No Drawings

ORGANIC SULFIDE ANTIOXIDANTS AND POLYMERS STABILIZED THEREWITH

FIELD OF THE INVENTION

The present invention is related to organic sulfide antioxidants which may be used to stabilize polyolefin resins against the detrimental effects of thermal and oxidative degradation both during processing and aging.

BACKGROUND OF THE INVENTION

Polyolefin resins, which are prepared from aliphatic olefins, are known in the art as a class of thermoplastics characterized by excellent physical properties. For example, polyolefin resins demonstrate a high resistance to stress cracking, a high tensile strength and a high stability under load. These physical properties make this class of thermoplastics particularly useful in the manufacture of pipe, film, wire, coated molded objects, etc.

However, polyolefins demonstrate a high amount of degradation at the high temperatures typically required in the processing of the polymers into useful finished articles. This drawback associated with the polyolefin resins is discussed, e.g., in U.S. Pat. No. 3,574,165.

Moreover, polyolefin resins are further detrimentally affected by oxidative degradation caused by the formation of peroxides in the polymer backbone. These peroxides decompose under the influence of heat and light initiating chain scission or crosslinking reactions in the polymer which ultimately result in the loss of physical properties. The compounds of this invention effectively decompose the peroxides before they can adversely affect the polymer.

In order to stabilize polyolefins against the deleterious effects of both thermal and oxidative degradation, it is known in the art to incorporate small amounts of various phenolic or arylamine antioxidants into the resin in combination with other antioxidants, such as sulfide containing antioxidants. For example, U.S. Pat. Nos. 3,180,850, 3,258,493, 3,293,209, 3,574,165, 3,652,680 and 3,772,246 all teach the use of a combination of these types of antioxidants as ingredients in resins to protect polyolefin resins from both thermal and oxidative degradation.

Conventional sulfide antioxidants, used to stabilize polyolefin resins, are the esters of thiodipropionic acid, particularly the dilauryl thiodipropionate and the distearyl thiodipropionate (DLTDP and DSTDP, respectively). Although the thiodipropionates are effective in stabilizing polyolefin resins, they suffer from the drawback of being hydrolytically unstable due to the presence of an ester functionality. Due to this hydrolytic instability, the thiodipropionates may be leached out of the polyolefin resins and articles made with these resins by hot water and in particular, hot water containing soap and detergents. The loss of the thiodipropionate stabilizer will cause premature deterioration, such as embrittlement and cracking of the polyolefins. This is particularly disadvantageous when the resins are used in hot water applications such as in hot water pipes, tubing applications and as components for automatic laundry and dishwashing equipment, etc. The drawbacks of the thiodipropionates are discussed in U.S. Pat. Nos. 3,652,680 and 3,772,246.

The present invention provides organic sulfide antioxidants which may be used to stabilize polyolefin resin compositions, which not only provide excellent results as antioxidants and processing stabilizers, but also possess hydrolytic stability. Moreover, the antioxidant compounds of the present invention may be incorporated into the polyolefin resins to protect the polyolefins both during processing and after the resins have been formed into articles.

SUMMARY OF THE INVENTION

The present invention relates to an organic sulfide antioxidant useful for stabilizing polyolefins against oxidative and thermal degradation during processing and use, the organic sulfide antioxidant being represented by Formula I:

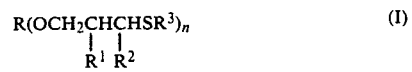

wherein n is an integer of 2 to 15;

R is a substituted or unsubstituted alkyl group of 2 to 30 carbons, a substituted or unsubstituted cycloalkyl group of 5 to 20 carbons, a substituted or unsubstituted alkyl group of 2 to 30 carbons where any of up to 6 carbon atoms are replaced with an O or S heteroatom, a substituted or unsubstituted cycloalkyl group of 5 to 20 carbons where any of up to 6 carbon atoms are replaced with an O or S heteroatom, with the proviso that the heteroatoms must be separated from each other and from the portion of the compound to which the R group is bonded by at least one carbon atom, the substituents for R being —OH, —SR$^4$ or —OR$^4$, wherein R$^4$ is an alkyl group of 1 to 30 carbons or a cycloalkyl group of 5 to 20 carbons;

R$^1$ and R$^2$ are independently H or an alkyl group of 1 to 4 carbons; and

R$^3$ is an alkyl group of 1 to 24 carbons or a cycloalkyl group of 5 to 20 carbons.

DETAILED DESCRIPTION OF THE PREFERRED EMBODIMENTS

The sulfide antioxidants of the present invention are those represented by Formula I set forth below:

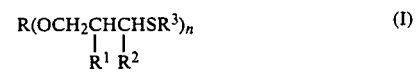

wherein n is an integer of 2 to 15;

R is a substituted or unsubstituted alkyl group of 2 to 30 carbons, a substituted or unsubstituted cycloalkyl group of 5 to 20 carbons, a substituted or unsubstituted alkyl group of 2 to 30 carbons where any of up to 6 carbon atoms are replaced with an O or S heteroatom, a substituted or unsubstituted cycloalkyl group of 5 to 20 carbons where any of up to 6 carbon atoms are replaced with an O or S heteroatom, with the proviso that the heteroatoms must be separated from each other and from the portion of the compound to which the R group is bonded by at least one carbon atom, the substituents for R being —OH, —SR$^4$ or —OR$^4$, wherein R$^4$ is an alkyl group of 1 to 30 carbons or a cycloalkyl group of 5 to 20 carbons;

R$^1$ and R$^2$ are independently H or an alkyl group of 1 to 4 carbons; and $R^3$ is an alkyl group of 1 to 24 carbons or a cycloalkyl group of 5 to 20 carbons.

Preferably, the present sulfide antioxidants are those represented by Formula I wherein R is $$CH_2-CH-CH_2, \quad -H_2C-\underset{\underset{CH_2-}{|}}{\overset{\overset{CH_2-}{|}}{C}}-CH_2-, \quad C_2H_5-\underset{\underset{CH_2-}{|}}{\overset{\overset{CH_2-}{|}}{C}}-CH_2-,$$

$$CH_3-\underset{\underset{CH_2-}{|}}{\overset{\overset{CH_2-}{|}}{C}}-CH_2-, \quad -CH_2-\underset{\underset{CH_2-}{|}}{\overset{\overset{CH_2-}{|}}{C}}-CH_2-O-CH_2-\underset{\underset{CH_2-}{|}}{\overset{\overset{CH_2-}{|}}{C}}-CH_2-,$$

$$-CH_2-\underset{\underset{CH_2-}{|}}{\overset{\overset{CH_2-}{|}}{C}}-CH_2-O-CH_2-\underset{\underset{CH_2-}{|}}{\overset{\overset{CH_2-}{|}}{C}}-CH_2-O-CH_2-\underset{\underset{CH_2-}{|}}{\overset{\overset{CH_2-}{|}}{C}}-CH_2-,$$

a mixture of:

[structures showing sorbitan/anhydro-sugar type rings with H and O substitutents]

wherein α and β are types of linkages $$H_2C-\underset{H}{\overset{H}{C}}-\underset{H}{\overset{|}{C}}-\underset{H}{\overset{|}{C}}-\underset{H}{\overset{|}{C}}-CH_2,$$

wherein
$R^1$ is H or $CH_3$;
$R^2$ is H; and
$R^3$ is an alkyl group of 10 to 18 carbons.

More preferably, the sulfide antioxidants of the present invention are those represented by Formula I wherein R is $$CH_2-CH-CH_2, \quad -CH_2-\underset{\underset{CH_2-}{|}}{\overset{\overset{CH_2-}{|}}{C}}-CH_2-, \quad C_2H_5-\underset{\underset{CH_2-}{|}}{\overset{\overset{CH_2-}{|}}{C}}-CH_2-,$$

$$CH_2-\underset{\underset{CH_2-}{|}}{\overset{\overset{CH_2-}{|}}{C}}-CH_2, \text{ and } -H_2C-\underset{H}{\overset{H}{C}}-\underset{H}{\overset{|}{C}}-\underset{H}{\overset{|}{C}}-CH_2-;$$

wherein
$R^1$ and $R^2$ are H; and
$R^3$ is an alkyl group of 12 to 18 carbons.

In the preferred and more preferred sulfide antioxidants set forth above, n is determined by the number of unattached bonds in each R group.

Preferred organic sulfide antioxidants in accordance with the present invention are pentaerythritol tetrakis(n-hexadecylthiopropyl)ether, pentaerythritol tris(n-hexadecylthiopropyl)ether, pentaerythritol tetrakis (n-octadecylthiopropyl) ether, pentaerythritol tris(n-octadecylthiopropyl) ether, pentaerythritol tetrakis (n-dodecylthiopropyl) ether, pentaerythritol tris(n-dodecylthiopropyl) ether, trimethylol propane tris(n-octadecylthiopropyl) ether, trimethylol propane tris(n-hexyldecylthiopropyl) ether, dipentaerythritol hexakis(n-octylthiopropyl) ether, dipentaerythritol hexakis (n-dodecylthiopropyl) ether and dipentaerythritol hexakis (n-hexyl decylthiopropyl) ether.

Examples of representative sulfide antioxidants useful in practicing the present invention are as set forth below:

$C_{18}H_{37}SCH_2CH_2CH_2O(CH_2CH_2O)_6CH_2CH_2OCH_2CH_2CH_2SC_{18}H_{37}$ $C_{16}H_{33}SCH_2CH_2CH_2O(CH_2CH_2SCH_2CH_2O)_2CH_2CH_2SCH_2CH_2OCH_2CH_2CH_2SC_{16}H_{33}$ $C_{12}H_{25}SCH_2\underset{\underset{CH_3}{|}}{CH}CH_2O(CH_2CH_2O)_4CH_2CH_2OCH_2\underset{\underset{CH_3}{|}}{CH}CH_2SC_{12}H_{25}$ $C_{14}H_{29}SCH_2CH_2CH_2OCH_2CH_2OCH_2CH_2OCH_2CH_2SCH_2CH_2OCH_2CH_2CH_2SC_{14}H_{29}$ $C_8H_{17}SCH_2\underset{\underset{CH_3}{|}}{CH}CH_2OCH_2CH_2OCH_2OCH_2CH_2SCH_2CH_2OCH_2\underset{\underset{CH_3}{|}}{CH}CH_2SC_8H_{17}$ $C_{13}H_{27}SCH_2CH_2CH_2O(CH_2CH_2CH_2CH_2O)_4CH_2CH_2CH_2CH_2OCH_2CH_2CH_2SC_{13}H_{27}$ $\begin{array}{l} H_2C-OCH_2CH_2CH_2SC_8H_{17} \\ HC-OCH_2CH_2CH_2SC_8H_{17} \\ H_2C-OCH_2CH_2CH_2SC_8H_{17} \end{array} \quad \begin{array}{l} H_2C-OCH_2CH_2CH_2SC_4H_9 \\ HC-OCH_2CH_2CH_2SC_4H_9 \\ H_2C-OCH_2CH_2CH_2SC_4H_9 \end{array}$ -continued $H_2C-OCH_2CH_2CH_2SC_{18}H_{37}$
$HC-OCH_2CH_2CH_2SC_{18}H_{37}$
$H_2C-OCH_2CH_2CH_2SC_{18}H_{37}$ $H_2C-OCH_2CH_2CH_2SC_{14}H_{29}$
$HC-OCH_2CH_2CH_2SC_{14}H_{29}$
$H_2C-OCH_2CH_2CH_2SC_{14}H_{29}$ $H_2C-OCH_2CH_2CH_2SC_{12}H_{25}$
$HC-OCH_2CH_2CH_2SC_{12}H_{25}$
$H_2C-OCH_2CH_2CH_2SC_{12}H_{25}$ $H_2C-OCH_2CH_2CH_2SC_{13}H_{27}$
$HC-OCH_2CH_2CH_2SC_{13}H_{27}$
$H_2C-OCH_2CH_2CH_2SC_{13}H_{27}$ $H_2C-OCH_2CH_2CH_2SC_{16}H_{33}$
$HC-OCH_2CH_2CH_2SC_{16}H_{33}$
$H_2C-OCH_2CH_2CH_2SC_{16}H_{33}$ $H_2C-OCH_2CH_2CH_2SC_{17}H_{35}$
$HC-OCH_2CH_2CH_2SC_{17}H_{35}$
$H_2C-OCH_2CH_2CH_2SC_{17}H_{35}$ $H_2C-OCH_2CH_2CH_2SC_9H_{19}$
$HC-OCH_2CH_2CH_2SC_9H_{19}$
$H_2C-OCH_2CH_2CH_2SC_9H_{19}$ $H_2C-O-CH_2CHCH_2SC_{10}H_{21}$
          $\quad\quad\quad CH_3$
$HC-O-CH_2CHCH_2SC_{10}H_{21}$
          $\quad\quad\quad CH_3$
$H_2C-O-CH_2CHCH_2SC_{10}H_{21}$
          $\quad\quad\quad CH_3$ $H_2C-OCH_2CHCH_2SC_8H_{17}$
      $\quad\quad CH_3$
$HC-OCH_2CHCH_2SC_8H_{17}$
      $\quad\quad CH_3$
$H_2C-OCH_2CHCH_2SC_8H_{17}$
      $\quad\quad CH_3$ $H_2C-OCH_2CHCH_2SC_{13}H_{27}$
      $\quad\quad CH_3$
$HC-OCH_2CHCH_2SC_{13}H_{27}$
      $\quad\quad CH_3$
$H_2C-OCH_2CHCH_2SC_{13}H_{27}$
      $\quad\quad CH_3$ $H_2C-OCH_2CHCH_2SC_{12}H_{25}$
      $\quad\quad CH_3$
$HC-OCH_2CHCH_2SC_{12}H_{25}$
      $\quad\quad CH_3$
$H_2C-OCH_2CHCH_2SC_{12}H_{25}$
      $\quad\quad CH_3$ $H_2C-OCH_2CH_2CHSC_{12}H_{25}$
          $\quad\quad CH_3$
$HC-OCH_2CH_2CHSC_{12}H_{25}$
          $\quad\quad CH_3$
$H_2C-OCH_2CH_2CHSC_{12}H_{25}$
          $\quad\quad CH_3$ $H_2C-OCH_2CHCH_2SC_{16}H_{33}$
      $\quad\quad CH_3$
$HC-OCH_2CHCH_2SC_{16}H_{33}$
      $\quad\quad CH_3$
$H_2C-OCH_2CHCH_2SC_{16}H_{33}$
      $\quad\quad CH_3$ $H_2C-OCH_2CHCH_2SC_{16}H_{33}$
      $\quad\quad C_3H_7$
$HC-OCH_2CHCH_2SC_{16}H_{33}$
      $\quad\quad C_3H_7$
$H_2C-OCH_2CHCH_2SC_{16}H_{33}$
      $\quad\quad C_3H_7$ $H_2C-OCH_2CHCH_2SC_{18}H_{37}$
      $\quad\quad CH_3$
$HC-OCH_2CHCH_2SC_{18}H_{37}$
      $\quad\quad CH_3$
$H_2C-OCH_2CHCH_2SC_{18}H_{37}$
      $\quad\quad CH_3$ $H_2C-OCH_2CH_2CH_2SC_{12}H_{25}$
$HC-OCH_2CHCH_2SC_{12}H_{25}$
      $\quad\quad CH_3$
$H_2C-OCH_2CH_2CH_2SC_{12}H_{25}$ $H_2C-OCH_2CHCH_2SC_{16}H_{33}$
      $\quad\quad CH_3$
$HC-OCH_2CH_2CH_2SC_9H_{19}$
$H_2C-OCH_2CH_2CH_2SC_9H_{19}$

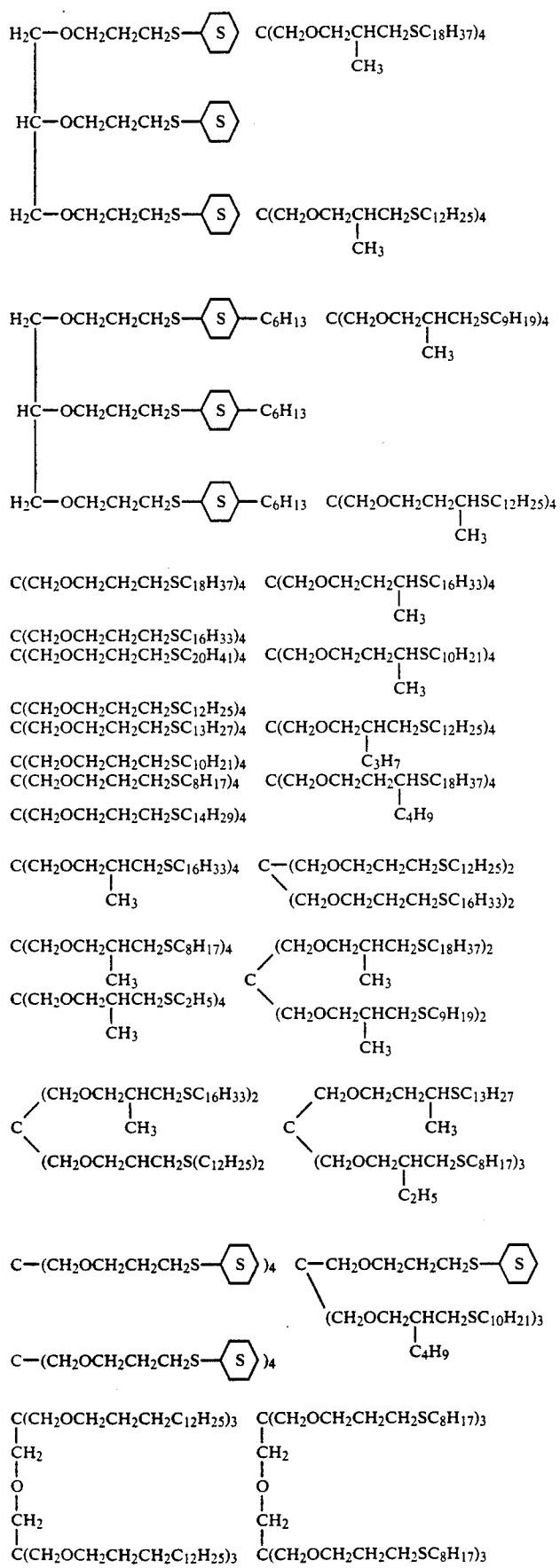

-continued

```
C(CH2OCH2CH2CH2C16H33)3      C(CH2OCH2CH2CH2SC9H19)3
|                             |
CH2                           CH2
|                             |
O                             O
|                             |
CH2                           CH2
|                             |
C(CH2OCH2CH2CH2C16H33)3      C(CH2OCH2CH2CH2SC9H19)3
```

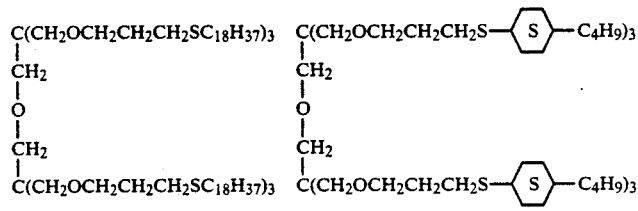

```
C(CH2OCH2CH2CHSCH3)3         C(CH2OCH2CH2CHSC6H13)3
|            |                |             |
CH2          CH3              CH2           CH3
|                             |
O                             O
|                             |
CH2                           CH2
|            |                |             |
C(CH2OCH2CH2CHSCH3)3         C(CH2OCH2CH2CHSC6H13)3
             |                              |
             CH3                            CH3
```

```
C(CH2OCH2CH2CH2SC10H21)3     C(CH2OCH2CHCH2SC12H25)3
|                             |            |
CH2                           CH2          CH3
|                             |
O                             O
|                             |
CH2                           CH2
|                             |            
C(CH2OCH2CH2CH2SC10H21)3     C(CH2OCH2CHCH2SC12H25)3
                                           |
                                           CH3
```

```
C(CH2OCH2CH2CH2SC20H41)3     C(CH2OCH2CHCH2SC9H19)3
|                             |            |
CH2                           CH2          CH3
|                             |
O                             O
|                             |
CH2                           CH2
|                             |
C(CH2OCH2CH2CH2SC20H41)3     C(CH2OCH2CHCH2SC9H19)3
                                           |
                                           CH3
```

```
C(CH2OCH2CH2CH2SC13H27)3     C(CH2OCH2CHCH2SC16H33)3
|                             |            |
CH2                           CH2          CH3
|                             |
O                             O
|                             |
CH2                           CH2
|                             |
C(CH2OCH2CH2CH2SC13H27)3     C(CH2OCH2CHCH2SC16H33)3
                                           |
                                           CH3
```

```
C(CH2OCH2CH2CH2SC11H23)3     C(CH2OCH2CHCH2SC18H37)3
|                             |            |
CH2                           CH2          CH3
|                             |
O                             O
|                             |
CH2                           CH2
|                             |
C(CH2OCH2CH2CH2SC11H23)3     C(CH2OCH2CHCH2SC18H37)3
                                           |
                                           CH3
```

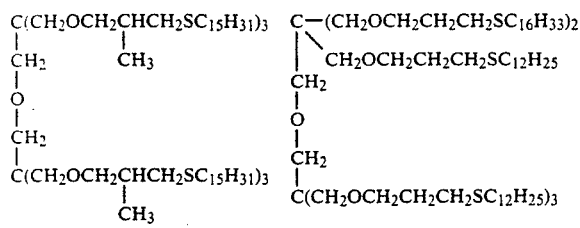
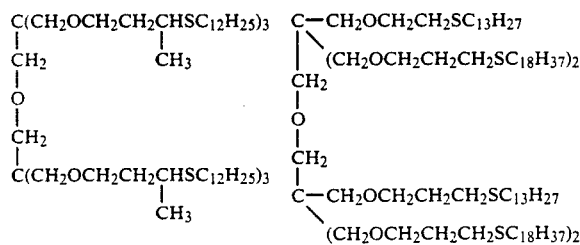
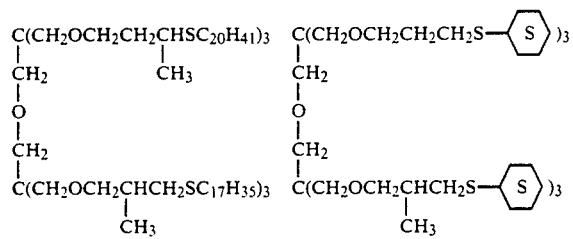
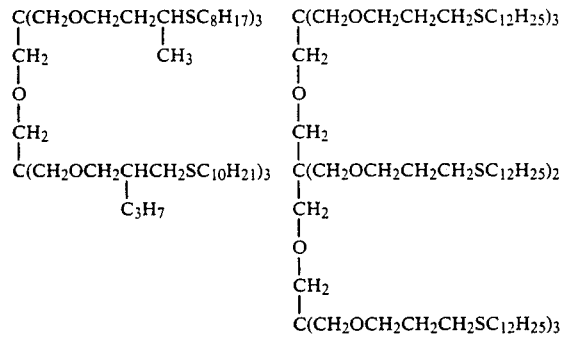
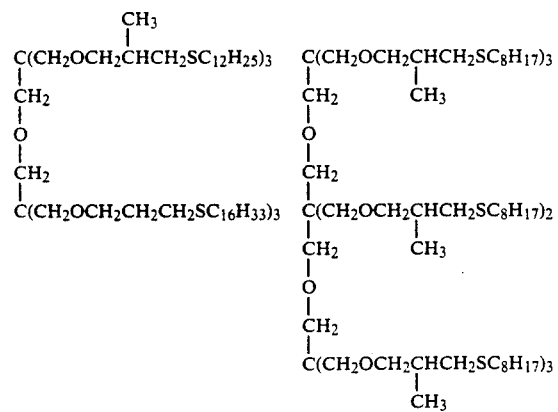

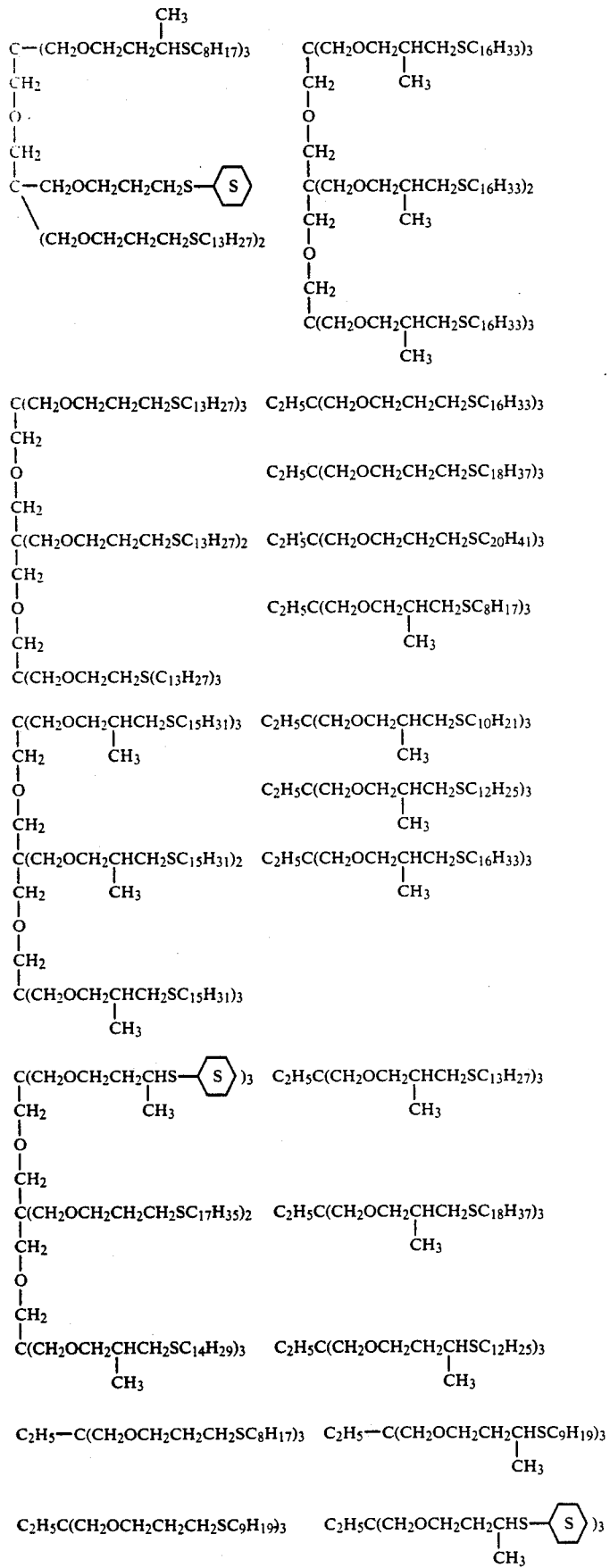

-continued $C_2H_5C(CH_2OCH_2CH_2CH_2SC_{10}H_{21})_3$ $C_2H_5C\begin{matrix}(CH_2OCH_2CH_2CH_2SC_{12}H_{25})_2\\CH_2OCH_2CH_2CH_2SC_{16}H_{33}\end{matrix}$ $C_2H_5C(CH_2OCH_2CH_2CH_2SC_{13}H_{27})_3$ $C_2H_5C\begin{matrix}(CH_2OCH_2CHCH_2SC_8H_{17})_2\\|\\C_4H_9\\CH_2OCH_2CHCH_2SC_{10}H_{21}\\|\\C_4H_9\end{matrix}$ $C_2H_5C(CH_2OCH_2CH_2CH_2SC_{14}H_{29})_3$ $CH_3C(CH_2OCH_2CH_2CH_2SC_{10}H_{21})_3$ $CH_3C\begin{matrix}(CH_2OCH_2CH_2CH_2SC_{12}H_{25})_2\\CHOCH_2CHCH_2SC_{12}H_{25}\\|\\CH_3\end{matrix}$ $CH_3C(CH_2OCH_2CH_2CH_2SC_8H_{17})_3$ $CH_3C(CH_2OCH_2CH_2CH_2SC_9H_{19})_3$ $CH_3C(CH_2OCH_2CH_2CH_2SC_{11}H_{23})_3$ $CH_3C(CH_2OCH_2CH_2CH_2SC_{12}H_{25})_3$ $CH_3C\begin{matrix}CH_2OCH_2CH_2CH_2SC_{10}H_{21}\\CH_2OCH_2CH_2CH_2SC_{12}H_{25}\\CH_2OCH_2CH_2CH_2SC_{16}H_{33}\end{matrix}$ $CH_3C(CH_2OCH_2CH_2CH_2SC_{13}H_{27})_3$ $CH_3C(CH_2OCH_2CH_2CH_2SC_{14}H_{29})_3$ $CH_3C(CH_2OCH_2CHCH_2SC_{12}H_{25})_3$
$|$
$C_3H_7$ $CH_3C(CH_2OCH_2CH_2CH_2SC_{16}H_{33})_3$ $CH_3C(CH_2OCH_2CH_2CH_2SC_{18}H_{37})_3$ $CH_3C(CH_2OCH_2CH_2CH_2SC_{19}H_{39})_3$ $\begin{matrix}CH_2OCH_2CH_2CH_2SC_{12}H_{25}\\HCO-CH_2CH_2CH_2SC_{12}H_{25}\\C_{12}H_{25}SCH_2CH_2CH_2O-CH\\HCO-CH_2CH_2CH_2SC_{12}H_{25}\\HCO-CH_2CH_2CH_2SC_{12}H_{25}\\CH_2OCH_2CH_2CH_2SC_{12}H_{25}\end{matrix}$ $CH_3C(CH_2OCH_2CHCH_2SC_8H_{17})_3$
$|$
$CH_3$ $CH_3C(CH_2OCH_2CHCH_2SC_{10}H_{21})_3$
$|$
$CH_3$ $\begin{matrix}CH_2OCH_2CH_2CH_2SC_{16}H_{33}\\HCO-CH_2CH_2CH_2SC_{16}H_{33}\\C_{16}H_{33}SCH_2CH_2CH_2O-CH\\HCO-CH_2CH_2CH_2SC_{16}H_{33}\\HCO-CH_2CH_2CH_2SC_{16}H_{33}\\CH_2OCH_2CH_2CH_2SC_{16}H_{33}\end{matrix}$ $CH_3C(CH_2OCH_2CHCH_2SC_{12}H_{25})_3$
$|$
$CH_3$ $CH_3C(CH_2OCH_2CHCH_2SC_{16}H_{33})_3$
$|$
$CH_3$ $CH_3C(CH_2OCH_2CHCH_2SC_{18}H_{37})_3$
$|$
$CH_3$ $\begin{matrix}CH_2OCH_2CH_2CH_2SC_{18}H_{37}\\HCO-CH_2CH_2CH_2SC_{18}H_{37}\\C_{18}H_{37}SCH_2CH_2CH_2O-CH\\HCO-CH_2CH_2CH_2SC_{18}H_{37}\\HCO-CH_2CH_2CH_2SC_{18}H_{37}\\CH_2OCH_2CH_2CH_2SC_{18}H_{37}\end{matrix}$ $CH_3C(CH_2OCH_2CH_2CHSC_{12}H_{25})_3$
$|$
$CH_3$ $CH_3C(CH_2OCH_2CH_2CHS\text{-}\underset{S}{\bigcirc}\text{-}C_6H_{13})_3$
$|$
$CH_3$ $\begin{matrix}CH_2OCH_2CH_2CH_2SC_8H_{17}\\HCOCH_2CH_2CH_2SC_8H_{17}\\C_8H_{17}SCH_2CH_2CH_2OCH\\HCOCH_2CH_2CH_2SC_8H_{17}\\HCOCH_2CH_2CH_2SC_8H_{17}\\CH_2OCH_2CH_2CH_2SC_8H_{17}\end{matrix}$ $\begin{matrix}CH_2OCH_2CH_2CH_2SC_9H_{19}\\HCOCH_2CH_2CH_2SC_9H_{19}\\C_9H_{19}SCH_2CH_2CH_2OCH\\HCOCH_2CH_2CH_2SC_9H_{19}\\HCOCH_2CH_2CH_2SC_9H_{19}\\CH_2OCH_2CH_2CH_2SC_9H_{19}\end{matrix}$ -continued
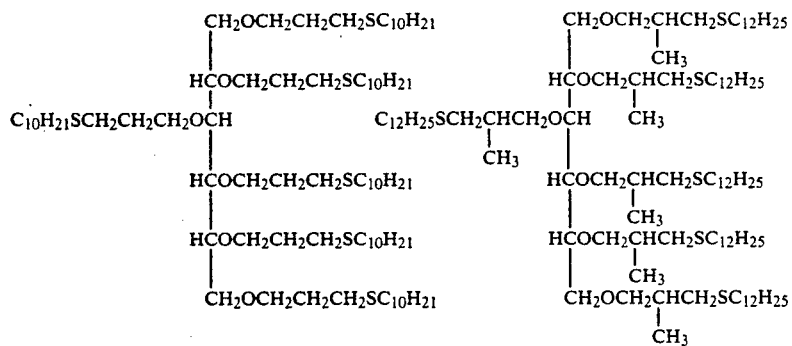
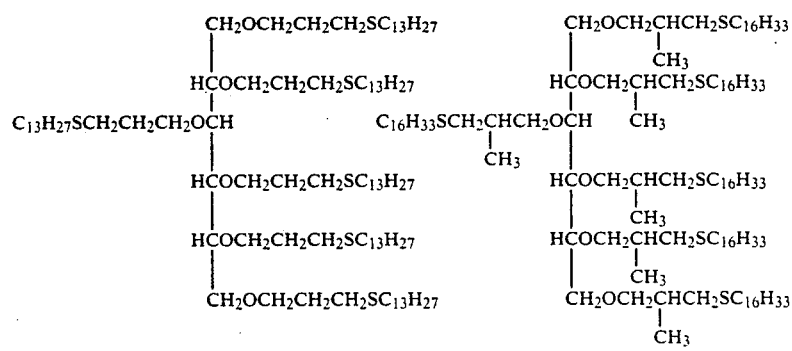
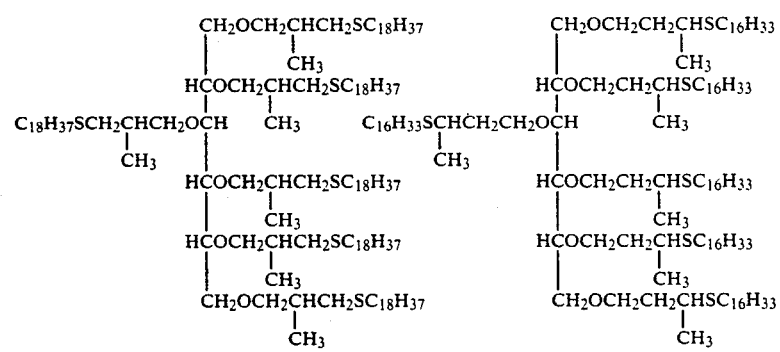
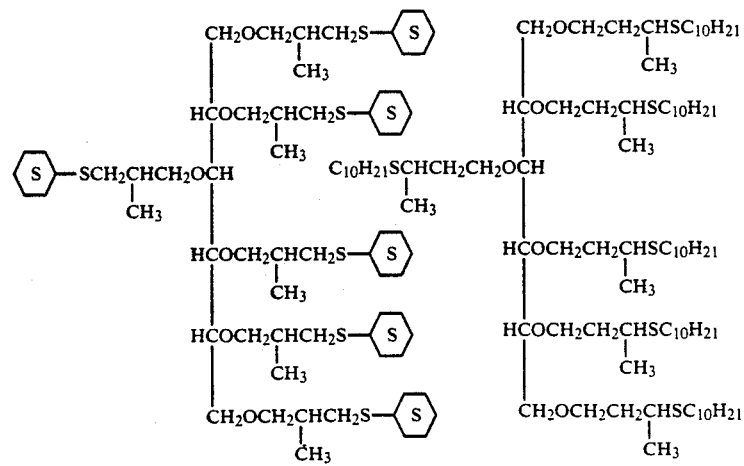

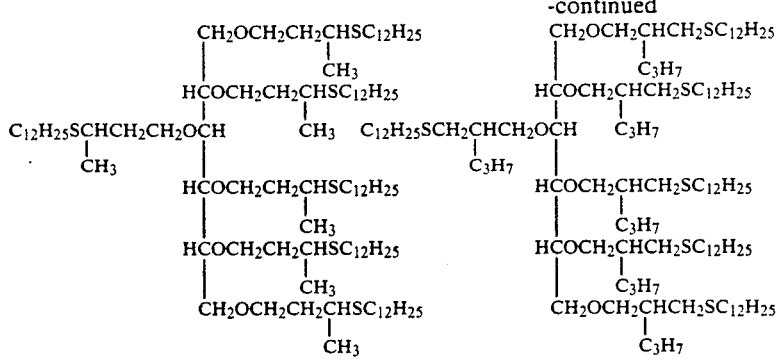

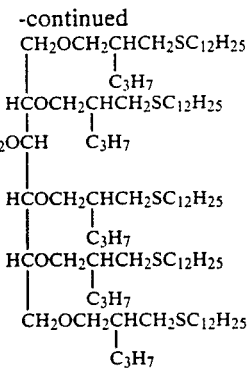

In the following non-limiting examples of representative structures for the sulfide antioxidants of the present invention, the sorbitan backbone shown is a 1,4-sorbitan, which comprises about 85% of the sorbitan of commerce. Sorbitan also contains about 13% of 3,6-sorbitan and about 2% of 2,5-anhydro-L-iditol (both isomers of 1,4-sorbitan). It will be understood by one skilled in the art that the sulfide antioxidants set forth below, which are derived from 1,4-sorbitan, also include these isomers.

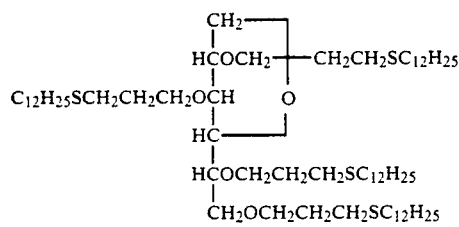

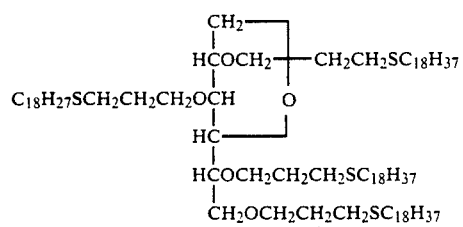

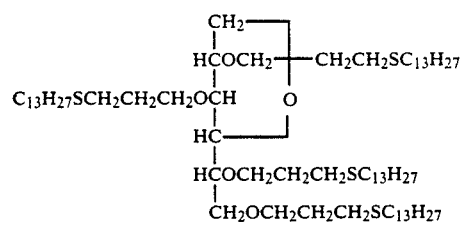

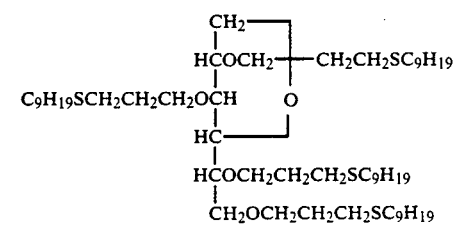

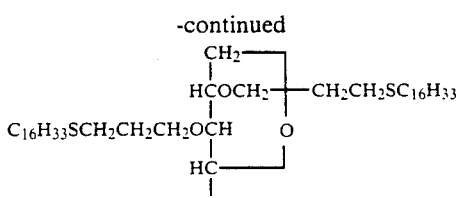

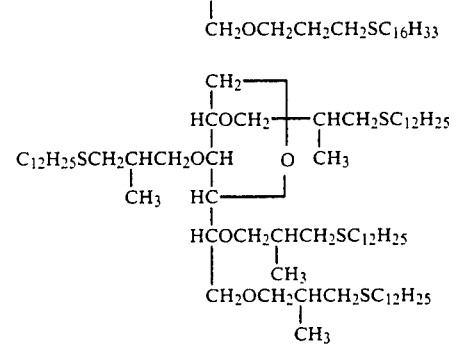

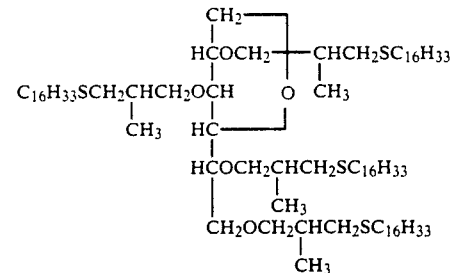

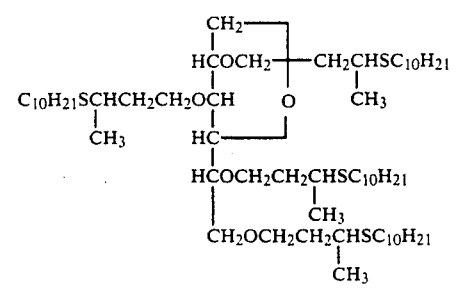

-continued
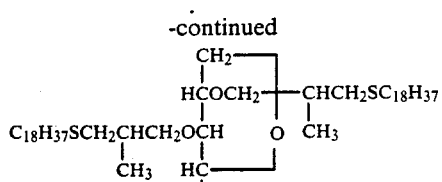
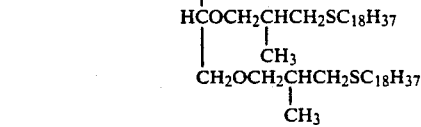
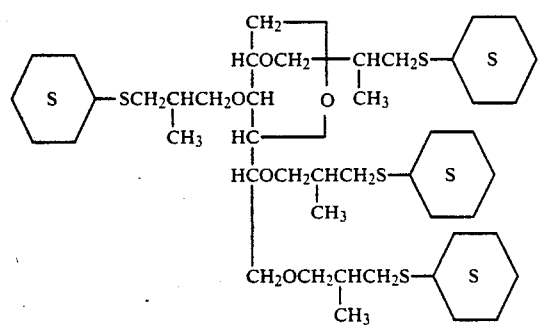
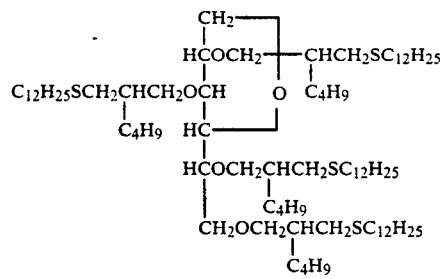
In the following non-limiting examples of representative sulfide antioxidants of the present invention derived from sucrose,
$Z$ is $CH_2CH_2CH_2SR^3$;
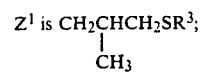
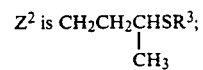
and $R^3$ is as defined above.
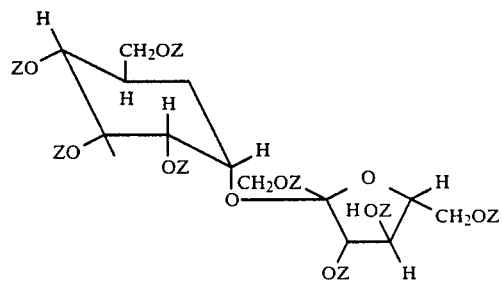
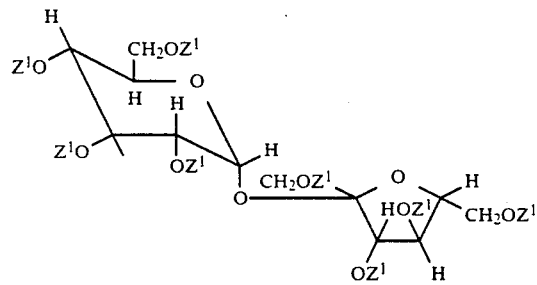
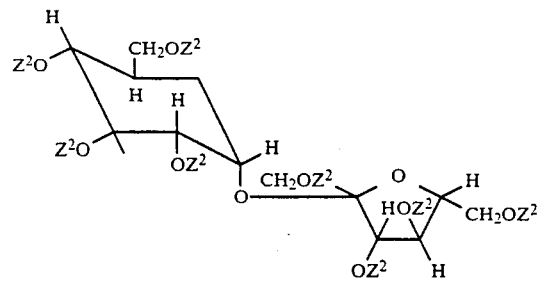
Non-limiting examples of the preferred sulfide antioxidants in accordance with the present invention are set forth below:
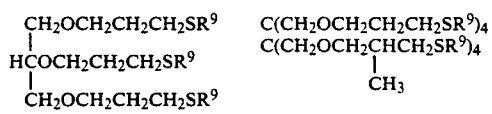
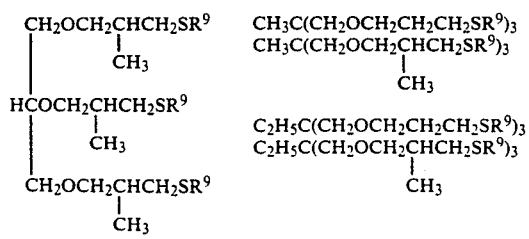
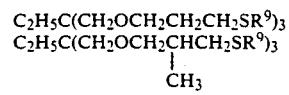

-continued
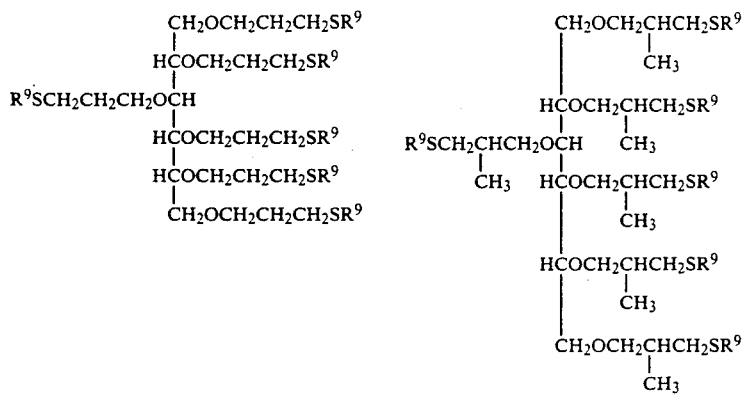
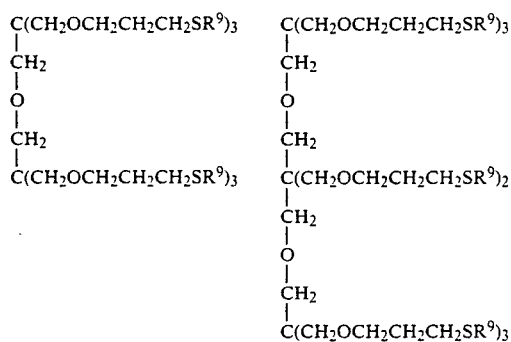
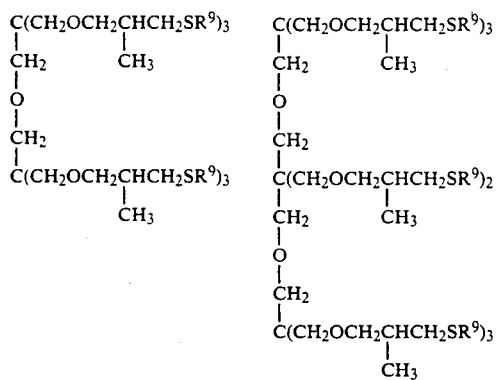
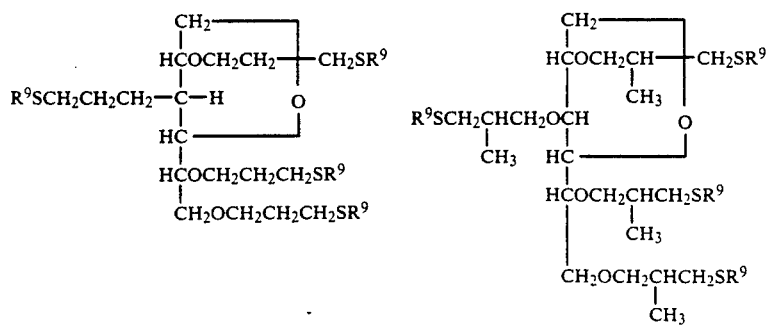

-continued

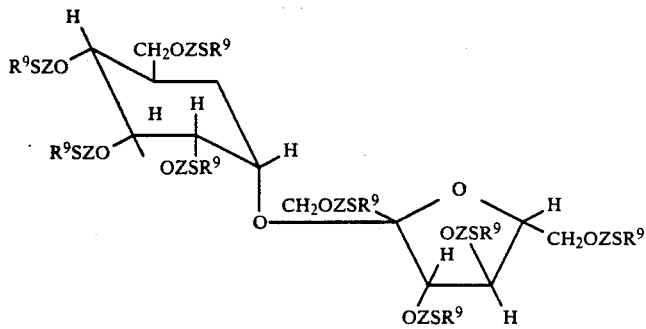

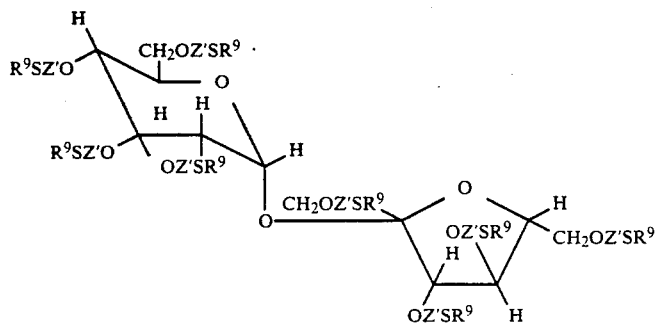

wherein $R^9$ represents an alkyl group of 10 to 18 carbons; $Z^4$ is $-CH_2CH_2CH_2-$, and $Z^5$ is

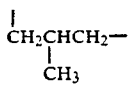

Non-limiting examples of the most preferred sulfide antioxidants in accordance with the present invention are set forth below:

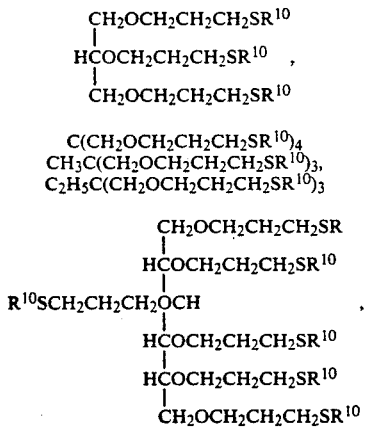

wherein $R^{10}$ represents an alkyl group of 12 to 18 carbons.

The organic sulfide antioxidants of the present invention represented by Formula I, may be prepared, for example, by first reacting a polyol (with two or more hydroxyl groups per molecule) with an allylic or substituted allylic halide (particularly chloride, bromide or iodide) in the presence of a base, such as sodium or potassium hydroxide. The amount of base used should be an amount sufficient to remove the by-product hydrogen halide and to form the corresponding polyallylic ether. Water or any other inert solvent may be used if necessary.

Next, a mercaptan is added, under free radical conditions (i.e., in the presence of peroxides, azo compounds, ultraviolet light, etc.) to the polyallylic ether discussed above, in order to form the antioxidant compounds of the present invention. The number of moles of mercaptan which should be employed in this reaction is an amount at least equal to the number of double bonds in the allyl ether. The present organic sulfide antioxidant compounds may also be prepared by other methods which will be evident to one skilled in the art based upon the present disclosure.

Illustrated below is a reaction scheme which may be used to prepare the compounds of the present invention.

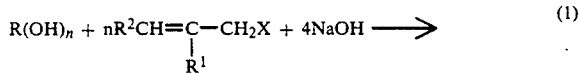

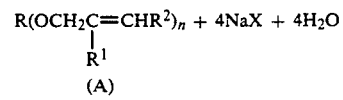

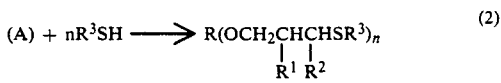

wherein R, $R^1$, $R^2$ and $R^3$ are as defined above and X is Cl, Br or I.

The sulfide antioxidants of the present invention may be added to a polyolefin resin in any conventional manner. Appropriate methods for the addition of the present compounds to a polyolefin resin will be evident to one skilled in the art based upon the present disclosure. For example, the present sulfide antioxidants may be added to the polyolefin resins by appropriate methods known in the art, such as blending, extruding, kneading, etc., with the requirement that a uniform mixture is produced.

The present organic sulfide antioxidants may be added to a polyolefin resin in synergistic combination with an auxiliary antioxidant, such as a phenolic or arylamine antioxidant.

Additives, such as talc, metal deactivators, calcium carbonate, calcium stearate, UV stabilizers (such as benzophenones, salicylic acid esters, hindered amines and benzotriazoles), etc., may further be added to a polyolefin resin composition containing the present organic sulfide antioxidants.

Generally, when used as stabilizers in polyolefin resins, the organic sulfide antioxidants of the present invention will be contained in the resin in an amount of about 1:10,000 to about 1:20, and preferably about 1:1,000 to about 7:1,000 parts by weight of antioxidant to resin. If an auxiliary antioxidant is used in combination with the sulfide antioxidants of the present invention, the weight ratio of primary antioxidant to the sulfide antioxidant is from bout 10:1 to about 1:10 and preferably about 1:2 to about 1:4.

The present invention will now be illustrated by reference to the following specific non-limiting examples.

EXAMPLE 1

Example 1 demonstrates the preparation of a mixture of pentaerythritol tetrakis(n-hexadecylthiopropyl) ether and pentaerythritol tris(n-hexadecylthiopropyl)ether.

A 250 ml three-necked flask equipped with a magnetic stirrer, a condenser and a nitrogen inlet tube was purged with nitrogen and charged with 91 g of n-hexadecyl mercaptan (0.35 mole). The n-hexadecyl mercaptan was then heated to 80° C. while stirred. To the heated and stirred n-hexadecyl mercaptan, 0.2 g of a solution of 2,2'-azobis(isobutyronitrile) in 26.49 of a 20/80 mixture of pentaerythritol tetra-allyl and triallyl ether (0.32 moles of unsaturation) was added dropwise over a 15-minute period.

One-half hour after the addition of the mixture was completed, 0.1 g of 2,2'-azobis(isobutyronitrile) was added. Two more 0.1 g additions of 2,2'-azobis-(isobutyronitrile ) were made at subsequent half-hour intervals. After the final addition of the 2,2'-azobis-(isobutyronitrile), the reaction mixture was held at 80° C. for one hour.

The product, a wax-like solid, was then recrystallized four times from 400 ml of isopropanol and 100 ml of hexane, yielding 41 g (38%) of a mixture of the pentaerythritol tetrakis(n-hexadecylthiopropyl) ether and pentaerythritol tris(n-hexadecylthiopropyl)ether. The recrystallized product was a white solid with a melting point range of 40°-48° C. NMR analysis indicated that the product was a mixture consisting of 40% of the tetrakis and 60% of the tris ethers.

An elemental analysis was conducted for $C_{81}H_{164}O_4S_4$ (tetrakis) (theoretical C, 73.12; H, 12.43; S, 9.64, OH, O); and $C_{62}H_{127}O_4S_3$ (tris) (theoretical C, 72.16; H, 12.30; S, 9.30; OH, 1.7).

The actual percentages found were: C, 73.3%; H, 12.5%; S, 9.26%; OH, 1.12%.

EXAMPLE 2

Example 2 demonstrates the preparation of pentaerythritol tetrakis(n-hexadecylthiopropyl) ether.

The procedure used was identical to that set forth in Example 1, except that 107 g of n-hexadecyl mercaptan (0.417 mole) was reacted with 29.64 g of pure pentaerythritol tetraallyl ether (0.1 mole). The crude product was recrystallized three times in 300 ml of hexane yielding 57 g of white solid having a melting point of 55°-57° C. An elemental analysis was conducted for $C_{88}H_{164}S_4O_4$ (theoretical C-73.12%, H-12.43%, S-9.64% and O-4.81%).

The actual percentages found were C-73.4%, H-11.9% and S-10.0%.

EXAMPLE 3

Example 3 demonstrates the preparation of pentaerythritol tetra(n-dodecylthiopropyl) ether.

The procedure used was identical to that set forth in Example 1, except that 123.9 g of n-dodecylmercaptan (0.612 mole) was reacted with 44.5 g of pentaerythritol tetraallyl ether (0.15 mole). The crude product was recrystallized twice in 800 ml of hexane yielding 95 g of a white solid having a melting point of 38°-40° C.

EXAMPLE 4

Example 4 demonstrates the preparation of pentaerythritol tetrakis(n-octadecylthiopropyl) ether.

The procedure used was identical to that set forth in Example 1, except that 119.4 g of n-octadecyl mercaptan (0.417 mole) was reacted with 29.6 g of pentaerythritol tetraallyl ether (0.1 mole). The crude product was then recrystallized three times in 300 ml of hexane yielding 54 g of a white solid having a melting point of 60°-63° C.

EXAMPLE 5

Example 5 demonstrates the preparation of trimethylolpropane tris(n-hexadecylthiopropyl) ether.

The procedure used was identical to that set forth in Example 1, except that 79.3 g of n-hexadecyl mercaptan (0.307 mole) was reacted with 25 g of trimethylol propane triallyl ether (0.0783 mole). The crude product was then recrystallized three times in 300 ml of hexane yielding 34 g of a white solid having a melting point of 39°-44° C.

EXAMPLE 6

Example 6 demonstrates the preparation of trimethylolpropane tris(n-octadecylthiopropyl) ether.

The procedure used was identical to that set forth in Example 1, except that 92.7 g of n-octadecyl mercaptan (0.323 mole) was reacted with 25 g of trimethylol propane triallyl ether (0.0983 mole). The crude product was recrystallized three times in 300 ml of hexane yielding 53 g of a white solid having a melting point of 43°-45° C.

EXAMPLE 7

Example 7 demonstrates the preparation of dipentaerythritol hexakis (n-octylthiopropyl) ether.

The procedure used was identical to that set forth in Example 1, except that 134.4 g of n-octyl mercaptan (0.919 mole) was reacted with 24.25 g of dipentaerythritol hexaallyl ether (0.15 moles). The crude product, an oil, was low-temperature recrystallized three times at −76° C. (in a dry ice/acetone bath) in 500 ml of hexane yielding 20 g of a clear oil.

EXAMPLE 8

Example 8 demonstrates the preparation of dipentaerythritol hexakis(n-dodecyl thiopropyl) ether.

The procedure used was identical to that set forth in Example 1, except that 123.9 g of n-dodecyl mercaptan (0.612 mole) was reacted with 49.5 g of dipentaerythritol hexaallyl ether (0.10 mole). The crude product, an oil, was low-temperature recrystallized three times at −10° C. in 500 ml of hexane yielding 38 g of a clear oil.

EXAMPLE 9

Example 9 demonstrates the preparation of dipentaerythritol hexakis(n-hexadecylthiopropyl) ether.

The procedure used was identical to that set forth in Example 1, except that 158.3 g of n-hexadecyl mercaptan (0.612 mole) was reacted with 49.5 g of dipentaerythritol hexaallyl ether (0.10 mole). The crude product, a solid, was recrystallized three times in 600 ml of hexane yielding 75 g of a white solid having a melting point of 44°-45° C.

EXAMPLES 10-22

Examples 10 to 22 illustrate the greater stability of the organic sulfide antioxidants of this invention in comparison to conventional sulfide antioxidants.

Small samples of antioxidants (10-25 mg) were heated in platinum boats at a rate 10° C. per minute. The temperature necessary to cause a weight loss of 5% was then determined. The gas flow (nitrogen or air) was 200 cc per minute in a duPont Model 9900 Thermogravimetric Analyzer.

Examples 10-14 are conventional antioxidants used in the plastics industry. The following antioxidants were used in Examples 10-14.

DLTDP-Dilauryl Thiodipropionate
DSPDPH-Distearyl Pentaerythritol Diphosphite
TBPBPH-Tetrakis(2,4-di-t-butylphenyl)-4,4'-biphenylene-diphosphonite
TBPP-Tris(2,5-di-t-butylphenyl) Phosphite The data set forth in Table I illustrates the temperature at which a 5% weight loss occurs for a series of antioxidants. Examples 15-22 are sulfide antioxidants in accordance with the present invention.

As can be seen from the Table I, the temperature at which a 5% weight loss occurs is considerably higher for the compounds according to the present invention as compared to conventional antioxidants. These results are consistent regardless of whether the analysis is run in the presence of air or nitrogen.

TABLE I

| | Thermogravimetric Analysis | |
|---|---|---|
| | | 5% Weight Loss (°C.) |
| Example No. | Antioxidant | Nitrogen | Air |
| 10 | DSTDP | 271 | 266 |
| 11 | DLTDP | 308 | 259 |
| 12 | DSPDPH | 252 | 259 |
| 13 | TBPBPH | 171 | 160 |
| 14 | TBPP | 291 | 280 |
| 15 | Product of Ex. 1 | 359 | 314 |
| 16 | Product of Ex. 2 | 368 | Not Evaluated |
| 17 | Product of Ex. 4 | 376 | Not Evaluated |
| 18 | Product of Ex. 5 | 374 | Not Evaluated |
| 19 | Product of Ex. 6 | 367 | Not Evaluated |
| 20 | Product of Ex. 7 | 365 | Not Evaluated |
| 21 | Product of Ex. 8 | 357 | Not Evaluated |
| 22 | Product of Ex. 9 | 359 | Not Evaluated |

EXAMPLE 23

Test specimens were made from 100 parts by weight of polypropylene, 0.1 parts by weight of pentaerythritol tetrakis[3,5-di-t-butyl-4-hydroxyhydrocinnamate], 0.1 parts by weight of calcium stearate and 0.3 parts by weight of additives.

A methylene chloride slurry of the ingredients was made and the solvent was evaporated. The resulting mixtures were then blended in an intensive mixer. The mixtures were then pelletized in a laboratory extruder at a temperature of 250° C.

The pellets were injection molded at 250° C. into test specimens (125 mil × ⅛ × 2½ inches).

The test specimens were aged in racks suspended from a slowly rotating Ferris wheel in a forced air oven at 150° C. Failure as noted in Table II set forth below was the time to formation of a discolored and friable area on the specimen.

TABLE II

| Additive | Avg. Days to Failure |
|---|---|
| None | 35 |
| DSTDP | 95 |
| Product of Ex. 1 | 141 |

The present invention may be embodied in other specific forms without departing from the spirit or essential attributes thereof and, accordingly, reference should be made to the appended claims, rather than to the foregoing specification as indicating the scope of the invention.

We claim:

1. An organic sulfide represented by Formula I:

$$R(OCH_2CHCHSR^3)_n \quad (I)$$
$$\phantom{R(OCH_2}|\phantom{CH}|$$
$$\phantom{R(OCH_2CH}R^1\phantom{CH}R^2$$

wherein n is an integer of 2 to 15;

R is a substituted or unsubstituted multivalent alkyl group of 3 to 30 carbons, a substituted or unsubstituted multivalent cycloalkyl group of 5 to 20 carbons, a substituted or unsubstituted multivalent alkyl group of 2 to 30 carbons where any of up to 6 carbon atoms are replaced with an O or S heteroatom, a substituted or unsubstituted multivalent cycloalkyl group of 5 to 20 carbons where any of up to 6 carbon atoms are replaced with an O heteroatom, with the proviso that the heteroatoms must be separated from each other and from the portion of the compound to which the R group is bonded by at least one carbon atom, the substituents for R being —OH, —SR$^4$ or —OR$^4$, wherein R$^4$ is an alkyl group of 1 to 30 carbons or a cycloalkyl group of 5 to 20 carbons;

R$^1$ and R$^2$ are independently H or an alkyl group of 1 to 4 carbons;

R$^3$ is an alkyl group of 1 to 24 carbons or a cycloalkyl group of 5 to 20 carbons.

2. An organic sulfide as in claim 1, wherein R is:

$$CH_2-CH-CH_2, \quad -H_2C-\underset{\underset{CH_2-}{|}}{\overset{\overset{CH_2-}{|}}{C}}-CH_2-, \quad C_2H_5-\underset{\underset{CH_2-}{|}}{\overset{\overset{CH_2-}{|}}{C}}-CH_2-,$$

$$CH_3-\underset{\underset{CH_2-}{|}}{\overset{\overset{CH_2-}{|}}{C}}-CH_2-, \quad -CH_2-\underset{\underset{CH_2-}{|}}{\overset{\overset{CH_2-}{|}}{C}}-CH_2-O-CH_2-\underset{\underset{CH_2-}{|}}{\overset{\overset{CH_2-}{|}}{C}}-CH_2-,$$

-continued

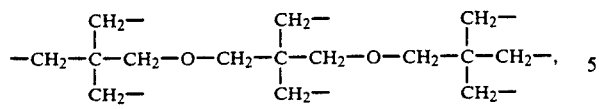

a mixture of:

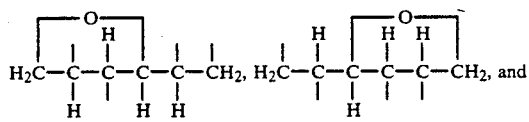

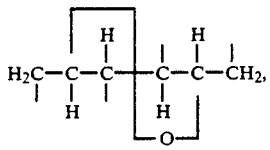

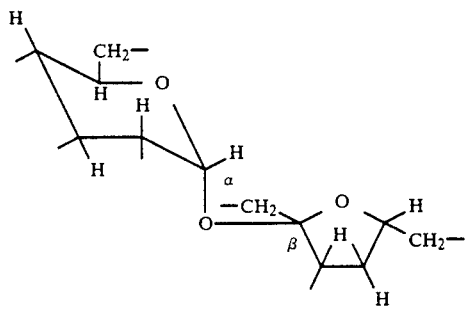

wherein α and β are the types of linkages, and

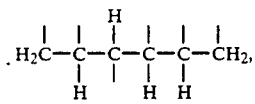

wherein
R¹ is H or CH₃;
R² is H;
R³ is an alkyl group of 10 to 18 carbons.
3. An organic sulfide as in claim 2, wherein R is

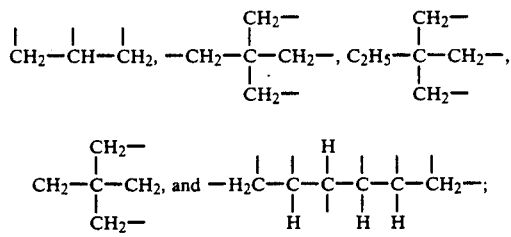

wherein
R¹ and R² are H;
R³ is an alkyl group of 12 to 18 carbons.
4. An organic sulfide antioxidant selected from the group consisting of

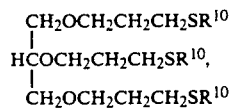

-continued
C(CH₂OCH₂CH₂CH₂SR¹⁰)₄,
CH₃C(CH₂OCH₂CH₂CH₂SR¹⁰)₃,
C₂H₅(CH₂OCH₂CH₂CH₂SR¹⁰)₃ and

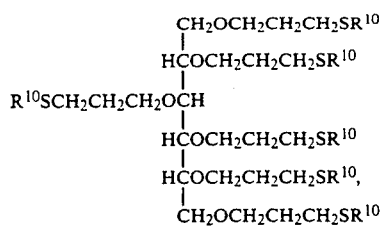

wherein:
R¹⁰ represents an alkyl group of 12 to 18 carbons.
5. An organic sulfide as in claim 1, having the name pentaerythritol tetrakis(n-hexadecylthiopropyl) ether.
6. An organic sulfide as in claim 1, having the name pentaerythritol tris(n-hexadecylthiopropyl) ether.
7. An organic sulfide as in claim 1, having the name pentaerythritol tetrakis(n-octadecylthiopropyl) ether.
8. An organic sulfide as in claim 1, having the name pentaerythritol tris(n-octadecylthiopropyl) ether.
9. An organic sulfide as in claim 1, having the name pentaerythritol tetrakis(n-dodecylthiopropyl) ether.
10. An organic sulfide as in claim 1, having the name pentaerythritol tris(n-dodecylthiopropyl) ether.
11. An organic sulfide as in claim 1, having the name trimethylol propane tris(n-octadecylthiopropyl) ether.
12. An organic sulfide as in claim 1, having the name trimethylol propane tris(n-hexyldecylthiopropyl) ether.
13. An organic sulfide as in claim 1, having the name dipentaerythritol hexakis(n-octyl thiopropyl) ether.
14. An organic sulfide as in claim 1, having the name dipentaerythritol hexakis(n-dodecylthiopropyl) ether.
15. An organic sulfide as in claim 1, having the name dipentaerythritol hexakis(n-hexyldecylthiopropyl) ether.
16. A method of stabilizing a polyolefin resin against oxidative or thermal degradation comprising adding to the resin an amount of an organic sulfide sufficient to stabilize the resin against oxidative or thermal degradation, the organic sulfide being represented by Formula I:

$$R(OCH_2CHCHSR^3)_n \quad (I)$$
$$\qquad\quad\; R^1 R^2$$

wherein
n is an integer of 2 to 15;
R is a substituted or unsubstituted multivalent alkyl group of 2 to 30 carbons, a substituted or unsubstituted multivalent cycloalkyl group of 5 to 20 carbons, a substituted or unsubstituted multivalent alkyl group of 2 to 30 carbons where any of up to 6 carbon atoms are replaced with an O or S heteroatom, a substituted or unsubstituted multivalent cycloalkyl group of 5 to 20 carbons where any or up to 6 carbon atoms are replaced with an O heteroatom, with the proviso that the heteroatoms must be separated from each other and from the portion of the compound to which the R group is bonded by at least one carbon atom, the substituents for R being —OH, —SR⁴ or —OR⁴, wherein R⁴ is an alkyl group of 1 to 30 carbons or a cycloalkyl group of 5 to 20 carbons;

R¹ and R² are independently H or alkyl group of 1 to 4 carbons;

R³ is an alkyl group of 1 to 24 carbons or a cycloalkyl group of 5 to 20 carbons.

17. A method according to claim 16 wherein the organic sulfide is present in an amount of about 1:10,000 to about 1:20 parts by weight of the resin.

18. A method according to claim 17 wherein the organic sulfide is present in an amount of about 1:1,000 to about 7:1,000 parts by weight of the resin.

19. A method according to claim 16 further comprising adding an auxiliary antioxidant to the resin.

20. A method according to claim 19 wherein the auxiliary antioxidant is selected from the group consisting of phenolic and arylamine antioxidants.

21. A method according to claim 20 wherein the auxiliary antioxidant is present in a weight ratio of auxiliary antioxidant to the organic sulfide of about 10:1 to about 1:10.

22. A method according to claim 21 wherein the weight ratio is about 1:2 to about 1:4.

23. A polyolefin stabilized against the oxidative or thermal degradation made by the method of claim 16.

* * * * *